United States Patent [19]

Goetz

[11] 4,104,746
[45] Aug. 8, 1978

[54] FOOT CRADLE

[76] Inventor: Verena M. Goetz, 80 Vernon Dr., Scarsdale, N.Y. 10583

[21] Appl. No.: 832,451

[22] Filed: Sep. 12, 1977

Related U.S. Application Data

[63] Continuation of Ser. No. 696,769, Jun. 16, 1976, abandoned.

[51] Int. Cl.$^2$ ............................................. A47C 21/00
[52] U.S. Cl. ...................................... 5/327 R; 5/338
[58] Field of Search ............... 5/317, 327 R, 337, 339; 269/323, 325; 297/427, 439

[56] References Cited

U.S. PATENT DOCUMENTS

| | | | |
|---|---|---|---|
| 1,481,038 | 1/1924 | Stephenson | 5/338 |
| 3,345,654 | 10/1967 | Noble | 5/327 R |
| 3,345,656 | 10/1967 | Steinman | 5/327 R |
| 3,931,654 | 1/1976 | Spann | 5/327 R |

*Primary Examiner*—Casmir A. Nunberg

*Attorney, Agent, or Firm*—James M. Rhodes, Jr.

[57] ABSTRACT

A foot support is herein described as having a base member for vertically supporting a patient's lower leg and foot above the level of the bed upon which the patient is lying. A sling is attached to the base to extend generally horizontally with respect thereto and to engage the underside of the patient's foot to prevent the base member from moving up the patient's leg.

In one form of the invention, the base member may have a horizontally extending opening for receiving the patient's lower leg. The opening may be sized to prevent the patient from horizontally withdrawing his leg and foot and a slot may be formed in the base member to extend from the periphery thereof to the opening. The patient may insert his lower leg and foot into the supported position within the opening by moving the lower leg portion transversely through the slot and into the base member opening. Multiple hook-like material fasteners may be used to secure the slot while the leg is being supported within the opening of the base member.

5 Claims, 5 Drawing Figures

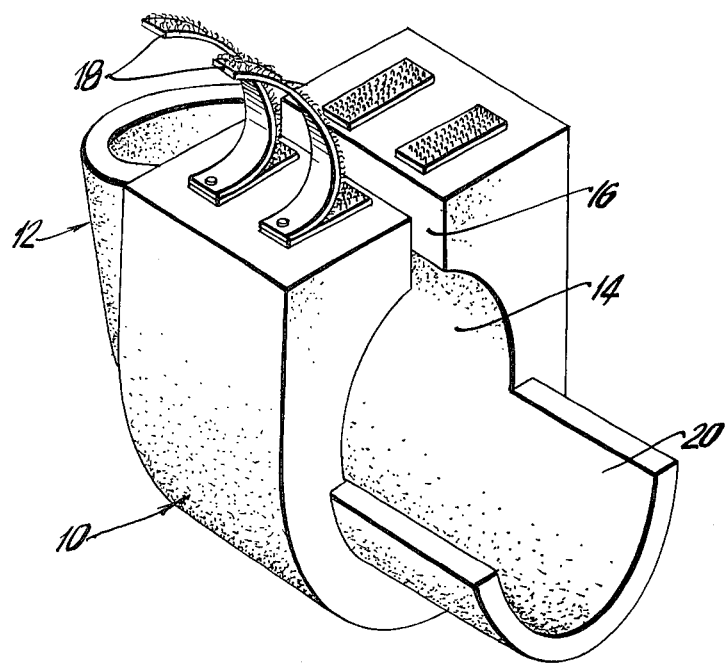
FIG. 3
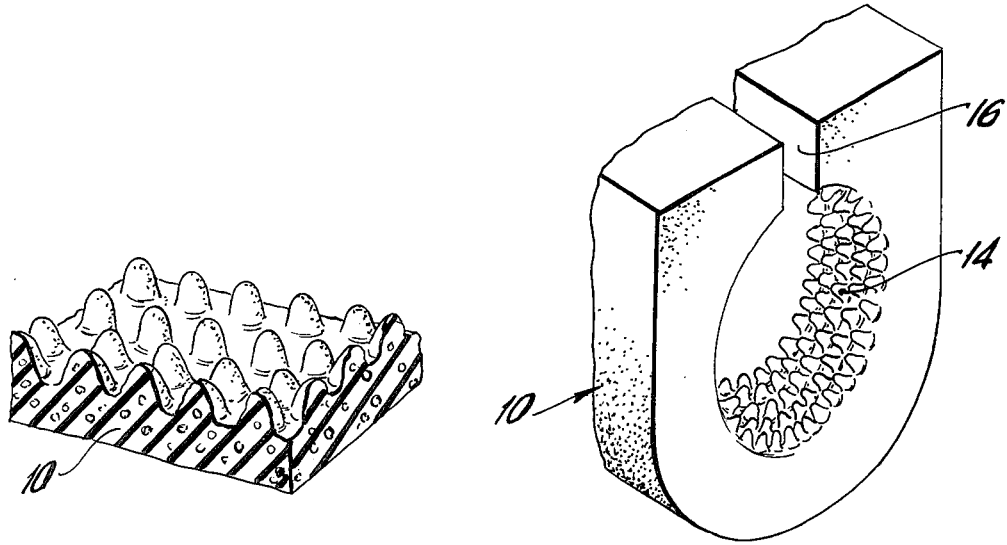
FIG. 4
FIG. 5

FOOT CRADLE

This is a continuation of application Ser. No. 696,769, filed June 16, 1976, now abandoned.

BACKGROUND OF THE INVENTION

The present invention relates to medical apparatus and, in particular, relates to apparatus for preventing decubitus necrosis during bed rest for any period in general and during the post operative period in particular.

Although modern surgical methods and existing apparatus for assisting post surgery recuperation have been greatly improved over the years, a patient who has poor blood circulation after serious surgery may develop gangrene because of excessive pressure created at various points on the patient's body as the patient is supported in bed. In particular, the back of the heel and malleoli of a patient's foot may have such pressure applied to it that the patient's existing poor circulation is further inhibited.

It would therefore be advantageous if an uncomplicated apparatus were provided for removing such an intensive pressure point and at the same time would slightly raise the patient's foot above the level of the bed in which he is lying so as to prevent decrease in circulation.

OBJECTS AND SUMMARY OF THE PRESENT INVENTION

It is, therefore, an object of the present invention to provide an apparatus for minimizing circulation inhibiting pressure points about a patient's foot and lower leg area during the post surgical recuperation period and during any period of inactivity such as sleep.

This object is achieved by the provision of a foot support including a base member for vertically supporting a patient's leg above the level of the horizontal surface upon which the patient is lying. The base member is formed to engage the patient's lower leg area just below the calf and above the malleoli. A sling member is attached to the base member to extend generally horizontally with respect to the base member and to engage the underside of the patient's foot. Through this arrangement, that portion of the patient's leg and foot (from approximately the patient's ankle down) is supported as a cantelever, free of pressure points which inhibit blood circulation. Most importantly, the sling member maintains the position of the support so that it does not slide up the patient's leg as does happen with existing supports, with the result that the heel once again bears on the surface of the bed.

THE DRAWINGS

While the invention is particularly pointed out and distinctly claimed in a concluding portion of the specification, a preferred embodiment of the present invention is disclosed in the following detailed description which may be best understood by reference to the following drawings in which:

FIG. 3 is a perspective view of the preferred embodiment of the present invention showing a pressure relieving pad feature; and FIGS. 4 and 5 are generally perspective representations of a nippled or studded surface defining the foot supporting portion of one form of the invention.

DETAILED DESCRIPTION

Figure 1:
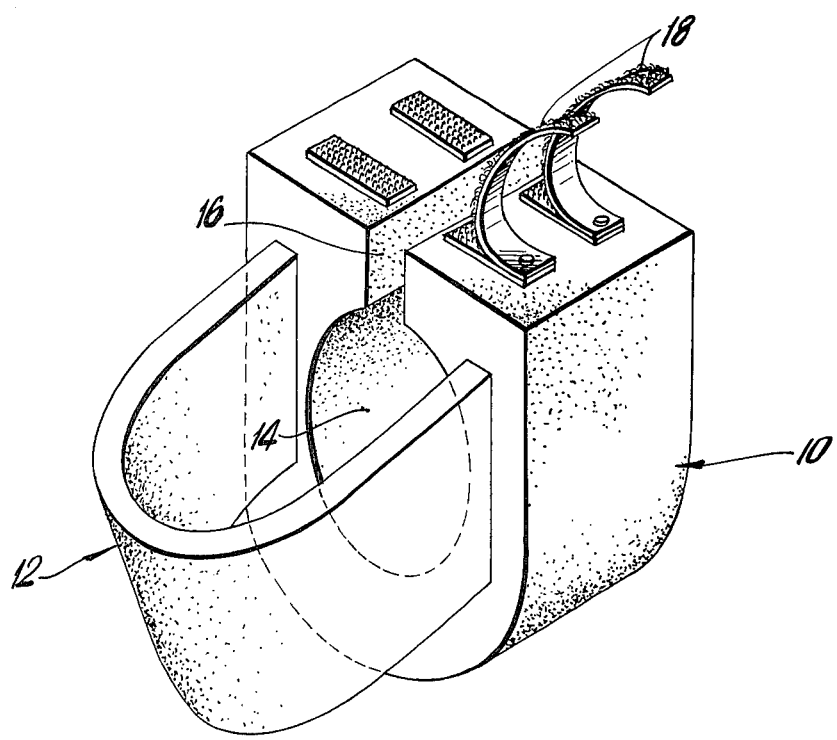
FIG. 1 is a perspective view of the preferred embodiment of the present invention.
Figure 2:
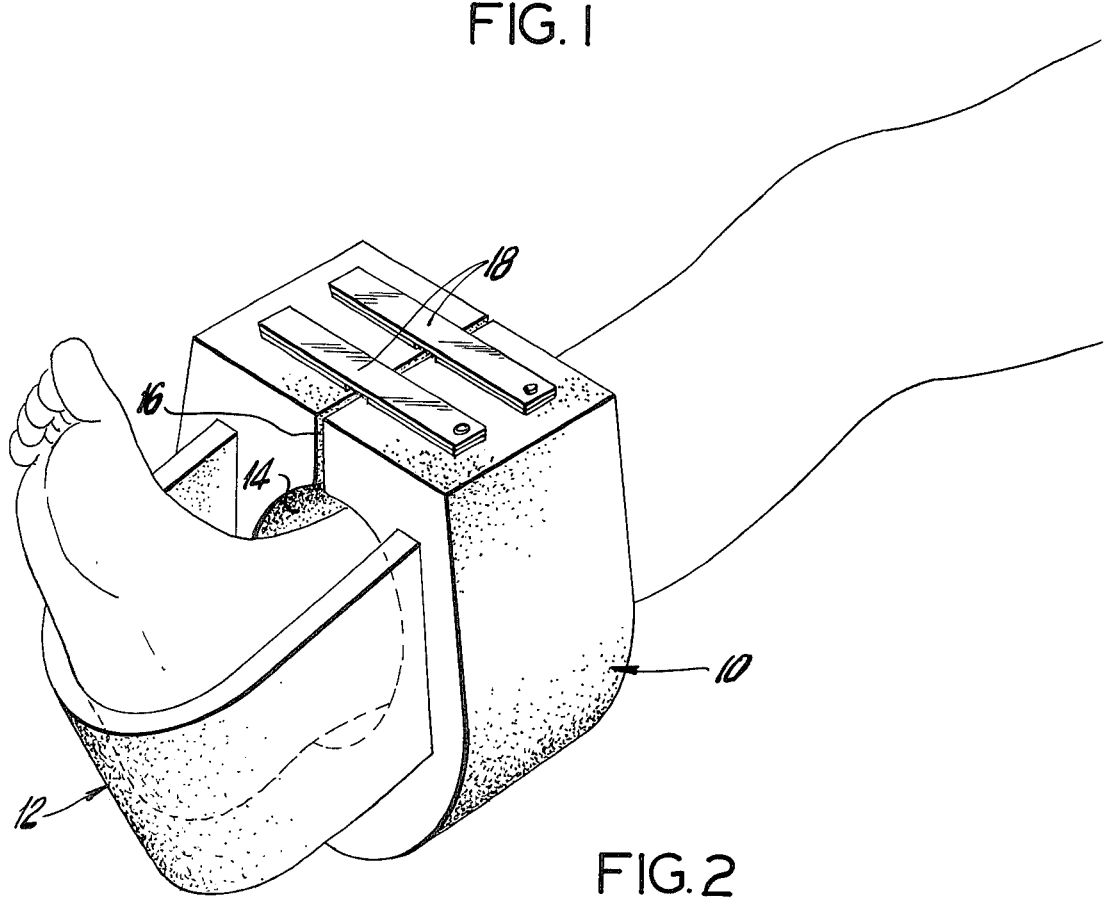
FIG. 2 is a perspective view of the preferred embodiment of the present invention in an operational posture.

Referring now to the drawings in which like numerals are used to indicate like parts throughout the various views thereof, the preferred embodiment of the present invention is shown in FIG. 1 to include a base member 10 for vertically supporting a patient's lower leg and foot. A sling member 12 is provided to engage the underside of a patient's foot as shown in FIG. 2 to prevent the support from riding up a patient's leg.

The base member may be generally U-shaped having a horizontally extending opening 14 for receiving the lower leg of a patient. The transverse dimension (the diameter in the illustrated support) may be approximately 8 centimeters which is large enough to circumscribe a typical patient's lower leg area, beneath the calf, but yet small enough to prevent the patient from horizontally withdrawing his foot through the opening 14. Of course, various sizes may be provided without departing from the invention.

A slot 16 may be formed to extend from the outer periphery of the base member to the opening 14 so that a patient may insert his lower leg transversely into the opening 14 through the slot 16.

The base member preferably comprises a soft though firm material such as foamed rubber or foamed urethane. While being supportive, the material must be sufficiently resilient to permit a patient to separate the surfaces of the base member defining the slot 16 for the transverse insertion of the patient's lower leg.

A holding device 18 is provided for preventing the slot 16 from opening in response to the application of the weight of the patient's leg to the surface defining the opening 14. The holding device may comprise multiple hook and loop fabric strips such as those currently available under the trademark VELCRO.

Referring now to FIG. 3, a generally arcuate, pressure relieving pad 20 may be provided adjacent the leg receiving opening 14 to prevent concentrated pressure to the ankle from the edge of the main body 10. The pad 20 may be of a foamed material and may be formed to extend horizontally in the direction opposite from the sling member 12.

Although various dimensions may be used in practicing the present invention, the inventor has found that if the leg receiving opening is centered at approximately 9 centimeters above the horizontal surface upon which the patient is lying, the present invention is particularly effective. It has been further found that a sling having a vertical height of 12 centimeters and in which the horizontal depth is approximately 15 centimeters is likewise especially effective. Of course, these dimensions will vary according to the firmness of the material comprising base 10.

In operation, the holding strips 18 are opened as shown in FIG. 1, and a patient's lower leg is transversely passed through the slot 16 into a supported position within the opening 14. The base member 10 is moved up the leg until the U-shaped sling 12 gently engages the underside of the patient's foot. The holding strips 18 are then closed so that the surface of the base member 10 defining the opening 14 gently engages about the patient's lower leg, just below the calf.

In one form of the invention, the internal surface defining the opening 14 in base member 10 may be formed of a nippled or studded configuration as opposed to a smooth surface. This surface configuration is indicated in FIG. 4 and operates to further distribute the pressure applied by a supported foot and lower leg.

While what has been shown herein is the preferred embodiment of the present invention, it is, of course, to be understood that various modifications and changes may be made therein without departing from the invention. It is, therefore, intended to cover in the following claims all such modifications and changes as may fall within the true spirit and scope of the present invention.

What is claimed is:

1. A foot support comprising:
    a base member formed of a generally pliable yet resilient and firm material for vertically supporting a patient's leg above the level of a horizontal surface upon which the patient is lying;
    said base member being formed with a generally horizontally extending opening for receiving a patient's leg and sized to prevent the horizontal removal of the patient's foot longitudinally therethrough, a slot being formed therein extending from the outer periphery of said base member to said opening so that the patient may insert his foot into said opening by passing his leg transversely through said slot;
    a sling member formed of a generally pliable yet resilient and firm material attached to said base member to extend at a gradually declining angle with respect to the vertical extensions of said base member and engageable with the underside of the patient's foot to prevent said base member from moving up the patient's leg;
    said opening in said base member being formed so that, when a patient's leg is disposed within said opening in a support posture, said sling member engages the underside of the patient's foot;
    said sling member and said base member being sized to engage only the foot and lower leg beneath the calf of a patient when worn thereby; and
    said foot support being unattached to any other structure, whereby a patient wearing said foot support may freely walk about while wearing said foot support.

2. A foot support according to claim 1, wherein at least the lower portion of the surface defining said opening is formed of a studded/nippled configuration to provide for the distribution of pressure applied to said base member by a supported foot.

3. A foot support according to claim 1, wherein said base member is generally U-shaped to define a generally arcuate base, whereby the patient wearing said foot support may freely roll upon said horizontal surface from his back to his side without any relative movement between said foot support and the foot of the patient.

4. A foot support according to claim 1, wherein a generally resilient pad is disposed adjacent the lower section of said opening to extend generally horizontally outwardly therefrom in a direction away from said sling member; said pad being operable to distribute pressure on a supported foot and lower leg.

5. A foot support according to claim 4, wherein said pad is of a generally arcuate configuration.

* * * * *